United States Patent [19]

Lippsmeier

[11] 3,984,448

[45] Oct. 5, 1976

[54] PRODUCTION OF DIALKYLTHIOPHOSPHATES

[75] Inventor: Bernhard Lippsmeier, Hurth-Knapsack, Germany

[73] Assignee: Hoechst Aktiengesellschaft, Frankfurt am Main, Germany

[22] Filed: Dec. 13, 1974

[21] Appl. No.: 532,411

[30] Foreign Application Priority Data

Dec. 20, 1973 Germany............................ 2363388

[52] U.S. Cl.......................... 260/429 R; 260/429.9; 260/435 R; 260/987; 260/429.5; 260/438.1
[51] Int. Cl.².......................... C07F 3/06; C07F 3/08; C07F 7/24
[58] Field of Search................ 260/970, 987, 429 R, 260/429.9, 435

[56] References Cited
UNITED STATES PATENTS 2,344,394    3/1944    Cook et al. ...................... 260/987 X

FOREIGN PATENTS OR APPLICATIONS 18,367    9/1963    Japan................................. 260/970

OTHER PUBLICATIONS

Houben–Weyl, Muller et al., Band XII/2, (1964) George Thieme Verlag, Stuttgart, p. 602.

*Primary Examiner*—Anton H. Sutto
*Attorney, Agent, or Firm*—Connolly and Hutz

[57] ABSTRACT

Production of dialkylthiophosphates of the general formula:

$$\left[ \begin{array}{c} R_1O \\ R_2O \end{array} \!\!\! >\!\! P(O)S \right]_n M$$

in which $R_1$ and $R_2$ stand for identical or different linear and/or branched alkyl radicals having from 1 to 6 carbon atoms, M stands for a metal cation and $n$ stands for the valence of the metal cation concerned, wherein O,O-dialkylphosphites of the general formula:

$$\begin{array}{c} R_1O \\ R_2O \end{array} \!\!\! \underset{H}{\overset{O}{>\!\!P\!\!<}}$$

in which $R_1$ and $R_2$ have the meanings given above, are reacted with a compound yielding the metal cation M, in the presence of pulverulent sulfur and organic solvents at elevated temperature, More particularly, high-grade and very pure dialkylthiophosphates are produced by using, as the compound yielding the metal cation M, the oxide of the corresponding mono- to tetravalent metal.

7 Claims, No Drawings

PRODUCTION OF DIALKYLTHIOPHOSPHATES

The present invention relates to a process for making dialkylthiophosphates of the general formula:

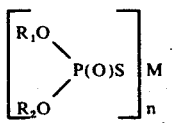

in which $R_1$ and $R_2$ stand for identical or different linear and/or branched alkyl radicals having from 1 to 6 carbon atoms, M stands for a metal cation and $n$ indicates the valence of the metal cation concerned, wherein O,O-dialkylphosphites of the general formula:

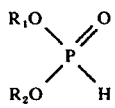

in which $R_1$ and $R_2$ have the meanings given hereinabove, are reacted with a compound yielding the metal cation M, in the presence of pulverulent sulfur and one or more organic solvents at elevated temperature.

It is known that alkali metal and alkaline earth metal dialkylthiophosphates can be produced by various processes, e.g. by subjecting thiophosphoric acid-O,O-diester chlorides to an alkaline hydrolysis, by reacting phosphoric acid diester-chlorides with hydrogen sulfides and by reacting ammonium-dialkylthiophosphates with soluble metal salts (cf. Houben-Weyl, vol. XII 2, pages 599 et seq. and 605 et seq.)

These known processes are seriously handicapped by the fact that the dialkylthiophosphates so made are always obtained together with metal salt by-products, normally alkali metal chlorides, from which they cannot be separated quantitatively, but at the price of very expensive and costly purification methods. It should be added that the above processes are substantially restricted to the manufacture of dimethyl and diethylthiophosphates, because of the limited availability of the necessary starting materials.

It has also been reported that alkali metal and ammonium dialkylthiophosphates can be made by reacting O,O-dialkylphosphites with sulfur and simultaneously with alkali metals, alkali metal alcoholates or alkali metal carbonates or ammonia (cf. German Pat. No. 1 050 330).

This latter process is not fully satisfactory, as it is substantially applicable to the production of alkali metal and ammoniumdialkylthiophosphates only. It should be added that in all those cases in which strong alkalies, such as alkali metals or alcoholates, are used, the O,O-dialkylphosphite is likely to undergo considerable decomposition with the resultant formation of the corresponding alkali metal or ammoniummonoalkylphosphites. In those cases in which alkali metal carbonates are used exclusively, the reaction mixture is subject to strong foaming, which is an additional handicap. A still further disadvantage resides in the fact that considerable quantities of alkali metal or ammonium-O,S-dialkylthiophosphates are obtained as by-products, which are very difficult to remove and cause considerable yield loss.

The present invention now unexpectedly provides a process for making dialkylthiophosphates of the general formula:

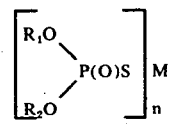

in which $R_1$ and $R_2$ stand for identical of different linear and/or branched alkyl radicals having from 1 to 6 carbon atoms, M stands for a metal cation and $n$ stands for the valence of the metal cation concerned, wherein O,O-dialkylphosphorous acid esters of the general formula:

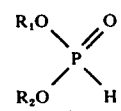

in which $R_1$ and $R_2$ have the meanings given hereinabove, are reacted with a compound yielding the metal cation M, in the presence of pulverulent sulfur and organic solvents at elevated temperature, which process comprises producing high-grade and very pure dialkylthiophosphates by using, as the compound yielding the metal cation M, the oxide of the corresponding mono- to tetravalent metal.

The useful oxides include more particularly those of copper, calcium, barium, magnesium, zinc, cadmium, titanium or lead, which may be used alone or in admixture with at most 50 weight % of the corresponding metal carbonates or basic metal oxides.

The organic solvents should preferably be selected from alcohols, ethers, aliphatic and aromatic hydrocarbons, and chlorinated saturated or unsaturated hydrocarbons. The reaction should more preferably be effected in accordance with the present invention in solvents in which the respective O,O-dialkylphosphite is readily soluble and in which the resulting reaction product is difficultly soluble. The sulfur should preferably be soluble at least partially in the particular solvent used. The preferred alcohols are those which correspond to the alkyl radicals $R_1$ and/or $R_2$ of the O,O-dialkylphosphites.

To bind the water formed during the reaction and to shorten the reaction period, it is good practice to use the reaction mixture in admixture with an equivalent proportion of a water-binding agent. The preferred agent is acetic anhydride as the resulting acetic acid is easy to separate.

It is also possible for toluene to be used as the solvent which simultaneously is an entrainer for the water formed, the latter being continually removed through a water separator.

The pulverulent sulfur should conveniently have a means particle size of less than 1 mm, preferably of less than 0.01 mm, as this enables the reaction period to be shortened.

The metal oxides should have a sufficiently high reactivity at the particular reaction conditions used. It is good practice to use oxides of bivalent to tetravalent metals, e.g. copper oxide, barium oxide, magnesium oxide, zinc oxide, cadmium oxide, lead oxide and titanium oxide. Blends of metal oxides with up to 50 weight % of the corresponding metal carbonates or basic metal oxides have also proved useful in some cases.

The use exclusively of metal carbonates or hydroxides should conveniently be avoided as this has been found to effect primarily the saponification of the respective phosphorous acid diester so that highly contaminated thiophosphates are obtained in poor yields.

The present invention has the particular merit of describing a reaction which is easy to carry out commercially and which produces high-grades material free from foreign substances.

The final product precipitates either directly or it is possible for it to be filtered off, washed and dried, after partial or complete separation of the solvent from the reaction mixture. It should be added that the metal oxides used in the process of the present invention are inexpensive starting material.

A further important advantage of the present process in which it compares very favorably with prior art methods, wherein relatively strongly contaminated alkali metal and ammoniumdialkylthiophosphates are obtained, resides in the fact that it is very useful for making a plurality of dialkylthiophosphates of other metals by the appropriate selection of the necessary starting materials.

The products of the present invention are very pure salts which are stable in solution and in solid form and which need not be purified for widespread uses in industry, for example as intermediates in the production of pesticides and pharmaceutical preparations. It is also possible for the very pure products of the present invention to be used for the stabilization of plastics, as corrosion inhibitors and paints. Still further, they can be used, alone or in combination with metal-O,O-dialkyl (aryl)dithiophosphates, which are produced from phosphorus pentasulfide and alcohols, as oil and lubricant additives, and they are useful aids in the textile, leather or paper industries.

The following Examples illustrate the process of the present invention.

EXAMPLE 1

1 mol (110 g) of dimethyl phosphite was diluted with 400 cc of methanol and the resulting solution was admixed with 1 mol (32 g) of pulverized sulfur (particle size: <0.1 mm). 0.5 mol (40.7 g) of zinc oxide was metered thereinto within 2 hours at 65°–67°C. The whole was stirred for 8 hours at that temperature to ensure quantitative reaction of the sulfur. The solvent was removed under vacuum and zinc dimethylthiophosphate, which was a viscous waxy material that could not be crystallized, was isolated. Zinc dimethylthiophosphate with a purity of 99 % was obtained in a yield of 124 g (90 %).

EXAMPLE 2

1 mol (32 g) of pulverized surfur (particle size: <1 mm) and 0.5 mol (40.7 g) of zinc oxide were dispersed in 600 cc of ethanol and 1.1 mol (151.8 g) of diethyl phosphite was added dropwise thereto within 1.5 hours at 79°C. During the addition of the phosphite, the temperature was within the range 79° and 80°C without supply of heat from the outside. To complete the reaction, the whole was maintained at 80°C with thorough agitation, for 6 hours. After cooling, 198.5 g of a colorless crystalline product was obtained, which was filtered off and dried. Traces of sulfur which adhered thereto were removed by treatment with a minor quantity of carbon disulfide. The whole was washed once with $CS_2$ and dried. 192.5 g of zinc diethylthiophosphate with a purity of 99.8 % was obtained. The compound melted at 3 163°–164°C.

EXAMPLE 3:

0.5 mol (62.2 g) of cadmium oxide and 1 mol (34 g) of pulverulent sulfur (particle size: <0.1 mm) were added to 350 cc of isobutanol. The whole was admixed first with 1 mol (102.1 g) of acetic anhydride and then, with thorough agitation at 100°C, with 1.1 mol (204 g) of di-isobutyl phosphite, which was added within 2 hours at temperatures within the range 100° and 108°C. The whole was allowed to further react for 4 hours at that temperature, then cooled and cadmium diisobutylthiophosphate crystallized out. After washing and drying, there was obtained 232 g of cadmium diisobutylthiophosphate melting between 207° and 208°C. The salt content was 99.7 %.

EXAMPLE 4

0.5 mol (40.7 g) of zinc oxide and 1 mol (32 g) of pulverized sulfur (particle size: <0.01 mm) were introduced into 600 cc of toluene. The whole was thoroughly mixed and 1.05 mols (174.0 g) of diisopropyl phosphite was added thereto within 2 hours at 110°C. The water formed during the reaction was removed through a water separator. The total reaction time was 8 hours. After cooling, a colorless salt precipitate was filtered off, washed and dried. 195 g of zinc diisopropylthiophosphate having a purity of 99.2 % and melting between 119° and 120°C was obtained.

EXAMPLE 5

0.5 mol (40.7 g) of zinc oxide and 1 mol (32 g) of pulverized sulfur (particle size: <0.01 mm) were added to 400 cc of isopropanol and the whole was admixed at 80°–85°C, with thorough agitation, with 1.1 mol (228.8 g) of n-hexyl-isopropylphosphite. After 6 hours of reaction at 80°C and removal of the solvent under vacuum, the zinc salt of O-n-hexyl-O-isopropylthiophosphoric acid was obtained in good yield.

EXAMPLE 6

The procedure was the same as that described in Example 2 save that a blend of zinc oxide and zinc carbonate in the ratio of 1 : 1 was substituted for pure zinc oxide. The reaction period was reduced from 7.5 to 6 hours. 190 g of zinc diethylthiophosphate having a purity of 99.8 % and melting between 163° and 164°C was obtained.

EXAMPLE 7

The procedure was the same as that described in Example 1 save that 1.1 mol (151.8 g) of diethylphosphite was substituted for the dimethylphosphite and a blend of lead oxide and lead carbonate (1 : 1) was substituted for zinc oxide. The solvent was ethanol. Lead diethylthiophosphate was obtained in good yield. The product, which could be recrystallized from hot water, had a purity of 99.2 % and melted at 45° to 46°C.

I claim:

1. In the process for making dialkylthiophosphates of the general formula:

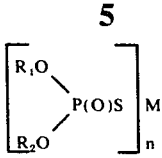

in which $R_1$ and $R_2$ stand for identical or different linear and/or branched alkyl radicals having from 1 to 6 carbon atoms, M stands for a metal cation and $n$ stands for the valence of the metal cation concerned, wherein O,O-dialkylphosphites of the general formula:

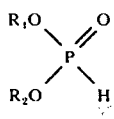

in which $R_1$ and $R_2$ have the meanings given above, are reacted with a compound yielding the metal cation M, in the presence of pulverulent sulfur and organic solvents at elevated temperature, the improvement which comprises reacting an oxide of zinc, cadmium or lead or either in admixture with at most 50 weight % of the corresponding metal carbonates or basic metal oxides as the compound yielding the metal cation M, with the remaining reaction compounds, whereby high grade and very pure dialkylthiophosphates are obtained.

2. The process as claimed in claim 1, wherein the reaction mixture is used in admixture with a water-binding agent or a solvent being a water entrainer.

3. The process as claimed in claim 2, wherein the water-binding agent is used in proportions approximately equivalent to the quantity of water formed during the reaction.

4. The process as claimed in claim 1, wherein the sulfur has a particle size smaller than 1 mm.

5. The process as claimed in claim 4, wherein the sulfur has a particle size smaller than 0.01 mm.

6. The process as claimed in claim 1, wherein the reaction is effected at temperatures within the range 25° and 150°C.

7. The process as claimed in claim 1, wherein the organic solvents are selected from alcohols, ethers, aliphatic or aromatic hydrocarbons, chlorinated, satured or unsaturated hydrocarbons.

* * * * *